(12) United States Patent
West et al.

(10) Patent No.: US 7,597,853 B2
(45) Date of Patent: Oct. 6, 2009

(54) METHOD AND APPARATUS FOR DISPENSING DIAGNOSTIC TEST STRIPS

(75) Inventors: Robert E. West, Basking Ridge, NJ (US); John Lovell, North Bergen, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 464 days.

(21) Appl. No.: 11/430,179

(22) Filed: May 9, 2006

(65) Prior Publication Data

US 2007/0264166 A1 Nov. 15, 2007

(51) Int. Cl.
*B01L 3/00* (2006.01)
(52) U.S. Cl. .......................... 422/102; 422/99
(58) Field of Classification Search ................. 422/104, 422/58, 68.1, 99, 102; 206/449, 569; 221/33, 221/65
See application file for complete search history.

(56) References Cited

U.S. PATENT DOCUMENTS

| | | | |
|---|---|---|---|
| 4,324,345 A | 4/1982 | Martinez | |
| 4,783,056 A | 11/1988 | Abrams | |
| 4,812,116 A | 3/1989 | Abrams | |
| 4,911,344 A | 3/1990 | Kahler | |
| 5,489,414 A | 2/1996 | Schreiber et al. | |
| 5,510,266 A | 4/1996 | Bonner et al. | |
| 5,632,410 A | 5/1997 | Moulton et al. | |
| 5,645,798 A | 7/1997 | Schreiber et al. | |
| 5,720,924 A | 2/1998 | Eikmeier et al. | |
| 5,723,085 A | 3/1998 | Abrams et al. | |
| 5,738,244 A | 4/1998 | Charlton et al. | |
| 5,810,199 A | 9/1998 | Charlton et al. | |
| 5,854,074 A | 12/1998 | Charlton et al. | |
| 5,863,800 A | 1/1999 | Eikmeier et al. | |
| 5,911,937 A | 6/1999 | Hekal | |
| 6,176,119 B1 | 1/2001 | Kintzig | |
| 6,213,343 B1 | 4/2001 | Damikolas | |
| 6,379,317 B1 | 4/2002 | Kintzig et al. | |
| 6,475,436 B1 | 11/2002 | Schabbach et al. | |
| 6,497,845 B1 | 12/2002 | Sacherer | |
| 6,872,358 B2 | 3/2005 | Hagen et al. | |
| 6,908,008 B2 | 6/2005 | Pugh | |
| 6,988,996 B2 | 1/2006 | Roe et al. | |
| 2003/0121932 A1 | 7/2003 | Wajda | |
| 2005/0017018 A1 | 1/2005 | Von Falkenhausen et al. | |
| 2005/0118071 A1* | 6/2005 | Sacherer ..................... 422/100 | |

FOREIGN PATENT DOCUMENTS

DE 30 01 332 7/1981
WO WO 2005/051822 6/2005

* cited by examiner

*Primary Examiner*—Jill Warden
*Assistant Examiner*—Jameson Q Ma
(74) *Attorney, Agent, or Firm*—Roylance, Abrams, Berdo & Goodman, L.L.P.

(57) ABSTRACT

An apparatus for storing and dispensing a test strip includes a container configured to store a radial array of test strips. The container maintains appropriate environmental conditions, such as humidity, for storing the test strips. The container has a plurality of radially extending slots formed by a plurality of dividing walls, and each slot is sized to receive a single test strip. A rotatably positionable cover is carried by the container for covering the plurality of radially extending slots. The cover includes an opening, which, when the cover rotates, aligns with one of the slots at a time to allow removal of a single test strip located within the respective slot. Accordingly, the unused test strips remain free of contaminants such as naturally occurring skin oils on a user's hand.

19 Claims, 8 Drawing Sheets

METHOD AND APPARATUS FOR DISPENSING DIAGNOSTIC TEST STRIPS

BACKGROUND OF THE INVENTION

1. Field of the Invention

The present invention generally relates to diagnostic test strips for testing biological fluids. More specifically, the present invention relates to an apparatus and method for storing and dispensing diagnostic test strips.

2. Background of the Invention

Diagnostic test strips are used to measure analyte concentrations in biological fluids. For example, diagnostic test strips are often used by diabetic patients to monitor blood glucose levels.

To preserve their integrity, diagnostic test strips must be maintained in appropriate environmental conditions. That is, the test strips should be maintained at appropriate humidity levels, and should remain free of foreign substances. Furthermore, to avoid contamination by skin oils or foreign substances, test strips should not be handled prior to use.

Thus, to preserve test strips, they are typically maintained in a storage vial or the like. In order to use a test strip, a user must reach into the vial, and retrieve a single test strip. However, many users, such as diabetic patients, have impaired vision or physical dexterity. Such users may find it difficult to retrieve a single test strip from a storage vial. Further, users may accidentally touch multiple test strips while reaching into the storage vial to withdraw a test strip, and potentially contaminate the unused test strips.

Accordingly, there is a need for an apparatus for storing diagnostic test strips in appropriate environmental conditions, and for conveniently dispensing the test strips one at a time.

SUMMARY OF THE INVENTION

An object of the present invention is to address at least the above problems and/or disadvantages and to provide at least the advantages described below. Accordingly, an object of the present invention is to provide an apparatus for storing a plurality of test strips and dispensing the test strips one at a time.

According to one embodiment of the present invention, the above and other objects are achieved by an apparatus for storing and dispensing a test strip which comprises a container including an outer wall and a plurality of radially extending slots formed by a plurality of dividing walls. Each slot is sized to receive a single test strip, and a rotatably positionable cover is carried by the container for covering the plurality of radially extending slots. The cover includes an opening so that when the cover rotates, the cover opening aligns with one of the slots at a time to allow removal of a single test strip located within the respective slot.

According to another embodiment of the present invention, an apparatus for storing and dispensing a test strip comprises a vial with a plurality of radially extending slots, each slot adapted to store a test strip, means for exposing one of the plurality of radially extending slots to dispense a test strip stored in the exposed slot, and means for actuating the exposing means.

According to still another embodiment of the present invention, a method for storing and dispensing test strips comprises the steps of storing a plurality of test strips in a radially arranged manner in a container, and covering the plurality of test strips in such a manner as to allow only one test strip at a time to be dispensed from the container.

BRIEF DESCRIPTION OF THE DRAWINGS

The above and other objects, features, and advantages of certain exemplary embodiments of the present invention will be more apparent from the following description taken in conjunction with the accompanying drawings, in which.

Throughout the drawings, the same reference numerals will be understood to refer to the same elements, features, and structures.

DETAILED DESCRIPTION OF EXEMPLARY EMBODIMENTS

Figure 1:
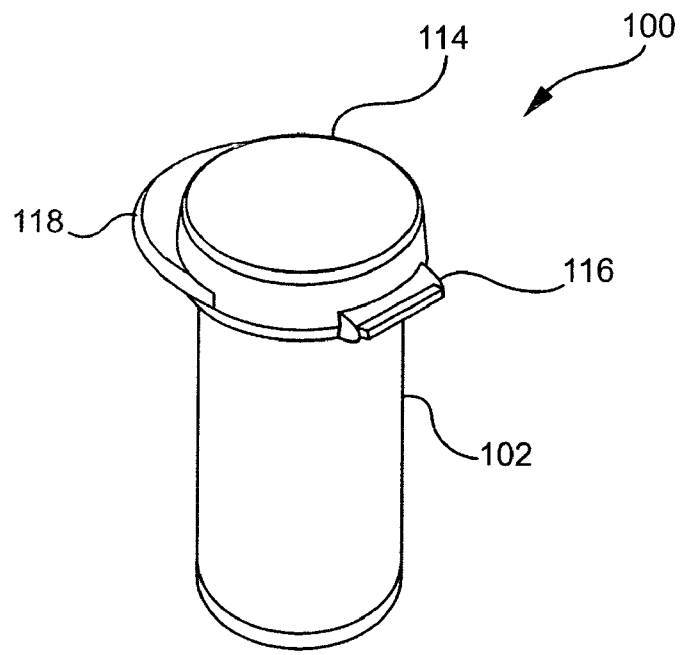
FIG. 1 is a perspective view of a storage vial for storing and dispensing test strips, according to a first exemplary embodiment of the present invention.

The matters defined in the description such as a detailed construction and elements are provided to assist in a comprehensive understanding of the embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

First Exemplary Embodiment

Referring to FIGS. 1-4, a storage vial 100 for storing and dispensing test strips according to a first exemplary embodiment of the present invention includes a container 102 with a plurality of radial slots 104 formed by a plurality of dividing walls 106. Each slot 104 is sized to receive one test strip 108. A rotatable cover 110 is positioned on top of the slots 104 to at least partially cover the plurality of slots 104 and prevent test strips received within the slots 104 from being removed from the slots 104. The rotatable cover 110 has a cover opening 112 which is sized to allow one test strip 108 to pass through the cover opening 112. The cover 110 may be rotated to align the cover opening 112 with one of the plurality of slots 104 to allow a test strip 108 located within the slot 104 to be dispensed.

As seen in FIG. 1, the container 102 may be provided with a lid 114 to prevent humidity and other environmental contaminants from entering the container 102. The lid 114 may be a separate detachable component, but preferably the lid 114 is connected to the container 102 by a hinge 116. In the illustrated embodiment, the lid 114 is formed integrally with the container 102 so that it is connected to the container 102 by a living hinge 116. The lid 114 preferably forms a substantially hermetic seal with the container 102. Such seals are known to those skilled in the art, and therefore, a detailed description of the seal will be omitted for conciseness. The lid 114 has an extended portion 118 which serves as a handle for a user to conveniently open the lid 114. For convenience of explanation, the lid 114 is only shown in FIG. 1.

Figure 2:
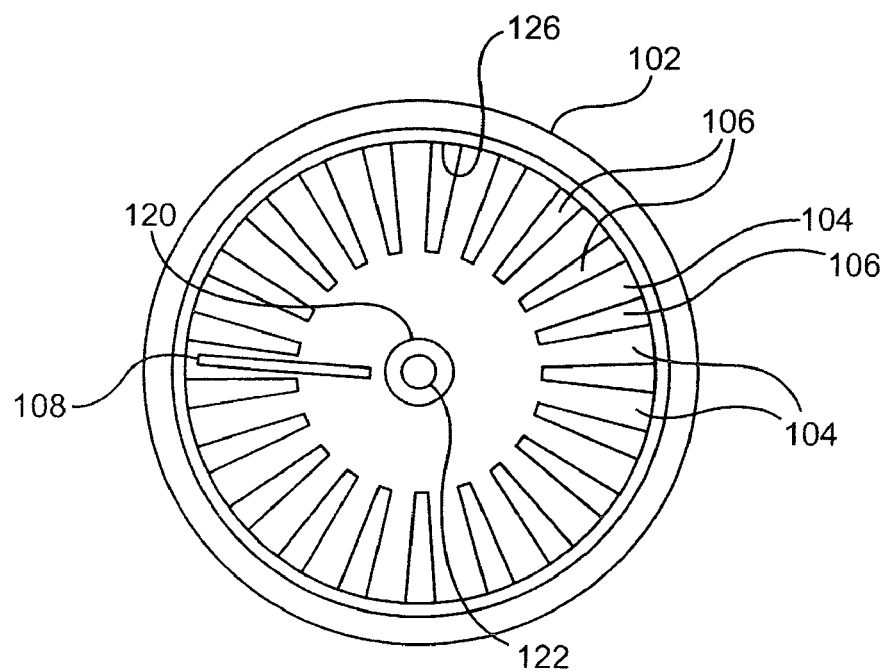
FIG. 2 is a top view of the container of the storage vial of FIG. 1, with the lid and rotatable cover both removed to expose the radial slots within the vial.

FIG. 2 is a top view of the container 102 after the lid 114 has been opened, with the rotatable cover 110 removed. The container 102 has a plurality of dividing walls 106 which form a plurality of slots 104. Each slot 104 is sized to receive one test strip. A boss 120 is located at the center of the container 102. The boss 120 has a recess 122. The recess 122 has an undercut portion (not illustrated) to cooperate with an elongated shaft 124 located on the rotatable cover 110, as will be described in further detail below.

Each of the dividing walls 106 extends radially inwardly from the outer wall 126 of the container 102. In an exemplary embodiment, the dividing walls 106 extend inwardly for approximately one-half (½) the width of a test strip. This allows a larger number of strips to be contained within the container 102 because each test strip does not need to be enclosed on all sides. It also allows each of the dividing walls 106 to have a substantially even wall thickness, thereby improving moldability. In the illustrated embodiment, the dividing walls 106 are formed integrally with the container 102. The dividing walls may, however, be formed separately as a sleeve to be inserted into the container 102, as will be described in further detail in connection with the second exemplary embodiment.

The dividing walls 106 may be formed of a desiccant entrained polymer to regulate the specific relative humidity within the container 102 (to prevent damage to humidity-sensitive test strips). U.S. Pat. No. 5,911,937, which is hereby incorporated by reference in its entirety, discloses one suitable desiccant entrained polymer. Forming the dividing walls 106 of a desiccant entrained polymer increases the exposed surface area of the desiccant entrained polymer, thereby improving humidity regulation within the container 102. Alternatively, the container 102 may be formed of a polymer with an insert-molded desiccant, or a desiccant may be placed in the bottom of the container 102, in the lid 114 of the container 102, or in one or more of the slots 104.

Figure 3:
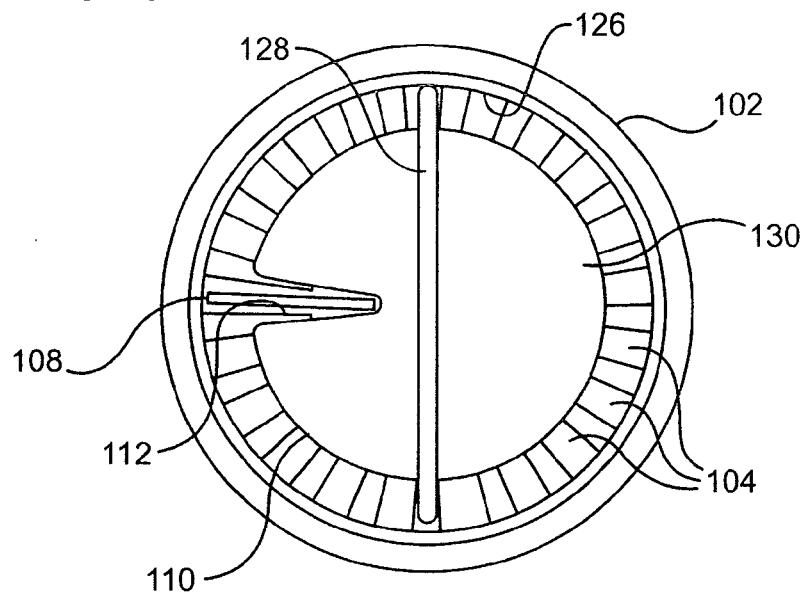
FIG. 3 is a top view of the container of FIG. 1, with only the lid removed to expose the rotatable cover.

FIG. 3 is a top view of the container 102 after the lid 114 has been opened, with the rotatable cover 110 shown in place. The cover 110 has a cover opening 112 which is sized to allow one test strip 108 to pass through the cover opening 112. The cover 110 has a handle to allow a user to grasp the cover 110 to rotate the cover 110. The outer diameter of the cover 110 is smaller than the inner diameter of the outer wall 126 of the container 102. This provides a gap between the outer wall 126 and the cover 110 so that a user may peer into the slots 104 in the container 102 and visually determine how many test strips are remaining in the container 102, and the placement of those test strips.

Figure 4:
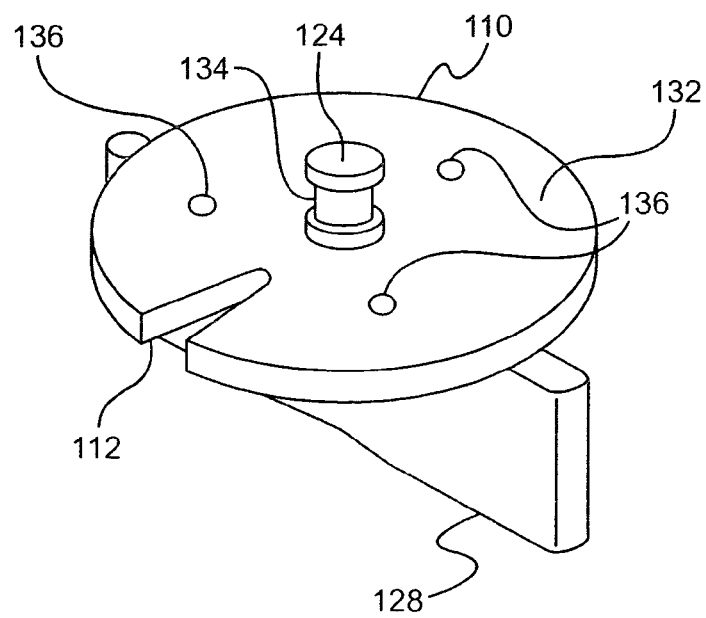
FIG. 4 is a bottom perspective view of the rotatable cover of the storage vial of FIG. 1.

FIG. 4 is a bottom perspective view of the rotatable cover 110. The cover 110 has an upper surface 130 and a lower surface 132. The lower surface 132 of the cover 110 has an elongated shaft 124. The elongated shaft 124 is configured so that it is positionable within the recess 122 located in the boss 120 in the container 102. Preferably, the elongated shaft 124 has an undercut portion 134 which cooperates with a mating portion (not illustrated) in the recess 122 of the boss 120. In this way, the elongated shaft 124 can be snap-fit into the boss 120.

The lower surface 132 of the cover 110 has detents 136 that engage the dividing walls 106 to control the rotation of the cover 110. In the illustrated embodiment, the detents 136 are formed by a plurality of extended protrusions. Preferably, the detents 136 are sized and positioned so that they align the cover opening 112 with one of the slots 104. The detents 136 also provide tactile feedback to a user indicating when the cover 110 has been rotated to the next slot 104.

The method of using the storage vial 100 for storing and dispensing test strips according to the first exemplary embodiment of the invention will now be described. Initially, test strips are loaded into the radially extending slots 104 formed in the container 102 so that one test strip is located in each slot 104. The rotatable cover 110 is then assembled to the container 102 by placing the elongated shaft 124 into the recess 122 in the boss 120. The elongated shaft 124 is retained in the recess by a snap-fit or the like. The lid 114 is then placed on the container 102 to form a substantially hermetic seal. The storage vial 100 may now be stored, and the test strips will be protected from environmental hazards, such as moisture. Typically, the foregoing steps will be performed by a manufacturer, rather than an end user of the storage vial 100.

To dispense a test strip, a user opens the lid 114 to expose the rotatable cover 110 and the cover opening 112. The user rotates the cover 110 by manipulating the cover handle 128, with the user's fingers or the like, so that the cover opening 112 is aligned with one of the slots 104. The detents located on the cover 110 provide assistance in aligning the cover opening 112 with one of the slots 104. When the cover opening 112 is aligned with a desired slot 104, a user then inverts the container 102. A test strip located within the slot 104 is dispensed through the cover opening 112 with the aid of gravity. The user may then grasp the dispensed test strip to withdraw the test strip from the container 102 and use the test strip. To dispense another test strip, the user rotates the cover 110 again to the next slot with an unused test strip. After dispensing the desired number of test strips, the user may then replace the lid 114 on the container 102 to store the remaining test strips for future use.

After all of the test strips stored in the container 102 have been dispensed, the storage vial 100 may be discarded, or may be returned to the manufacturer for recycling. Reusable embodiments of the container 102 are also within the scope of the present invention.

Second Exemplary Embodiment

Referring to FIGS. 5-16, a storage vial 200 for storing and dispensing test strips according to a second exemplary embodiment of the present invention includes a container 200 with a plurality of radial slots 204 formed by a plurality of dividing walls 206. Each slot 204 is sized to receive one test strip 208. A rotatable spinner 210 forms a cover which is positioned on top of the slots 204 to at least partially cover the plurality of slots 204 and prevent test strips received within the slots 204 from being removed from the slots 204. The spinner 210 has a cover opening 212 which is sized to allow one test strip to pass through the cover opening 212. The spinner 210 is rotated by a pushbutton 214. Each time the pushbutton 214 is pressed, the spinner 210 rotates so that the cover opening 212 is aligned with a new radial slot 204. Once the spinner 210 is aligned with a slot 204 containing a test strip, a user may invert the container 200 to dispense the test strip.

Figure 5:
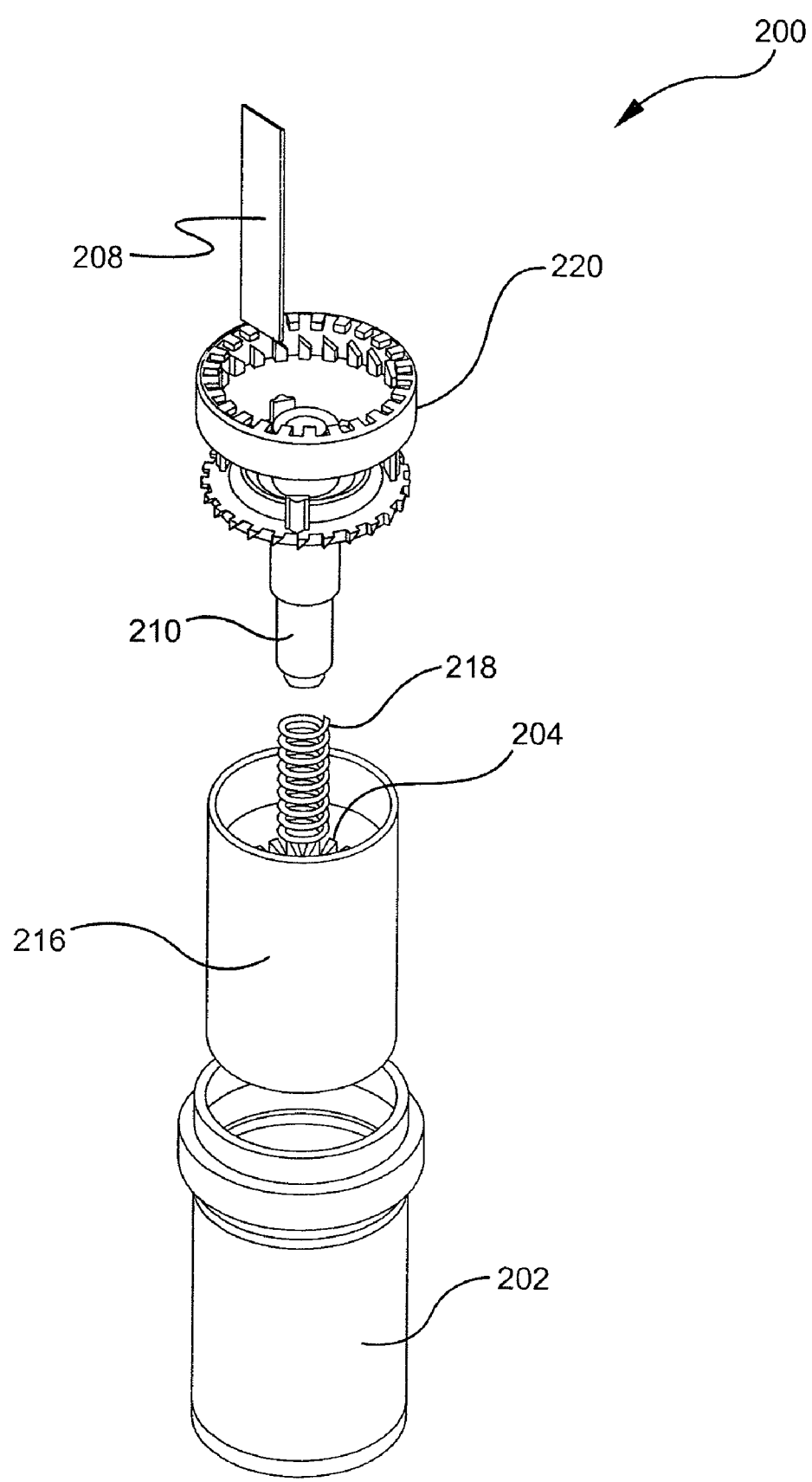
FIG. 5 is an exploded perspective view of a storage vial for storing and dispensing test strips, according to a second exemplary embodiment of the present invention.

Referring to FIG. 5, the storage vial 200 includes a container 200, a sleeve 216, a biasing element 218, a spinner 210, and a cam sleeve 220.

The container 200 is preferably formed of a substantially vapor impermeable material. The container 200 has a lid (not shown) which is substantially similar to the lid described with respect to the first embodiment.

Figure 7:
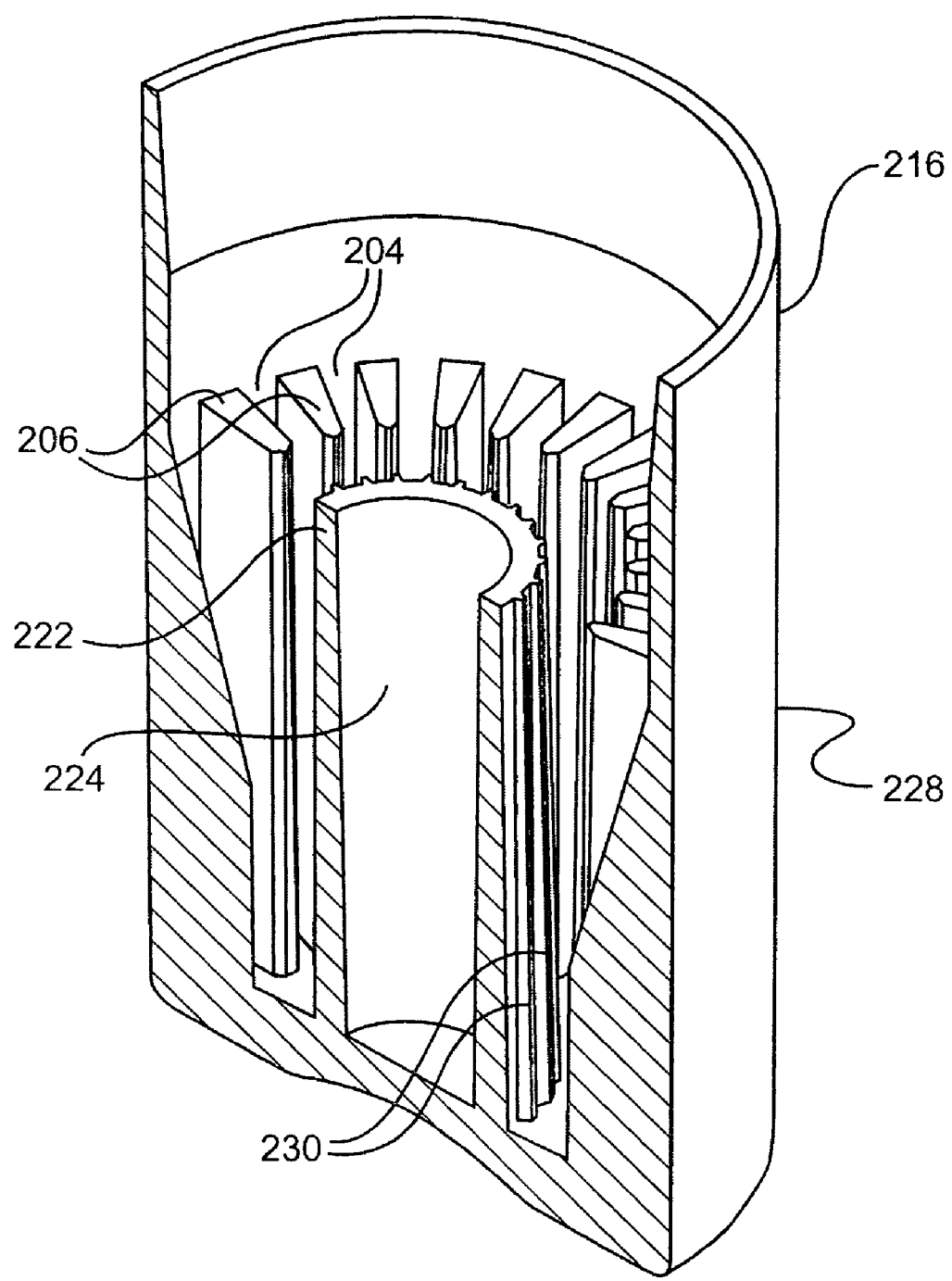
FIG. 7 is a cut-away perspective view of the sleeve of the storage vial of FIG. 5.

Referring to FIG. 7, the sleeve 216 has a plurality of dividing walls 206 which form a plurality of slots 204. Each slot 204 is sized to receive one test strip. A boss 222 is located at the center of the sleeve 216. The boss 222 has a recess 224. The recess 224 receives an elongated shaft 226 located on the spinner 210, as will be described in further detail below.

Each of the dividing walls 206 extends radially inwardly from the outer wall 228 of the sleeve 216. In an exemplary embodiment, the dividing walls 206 extend inwardly for approximately two-thirds (⅔) the width of a test strip, for the reasons discussed above with respect to the first embodiment. A plurality of guiding ribs 230 may be formed on the outer surface of the boss 222. The guiding ribs 230 help align test strips in the slots 204 to prevent the test strips from becoming misaligned. The outer diameter of the sleeve 216 is sized so that it fits snugly within the container 200.

Preferably, the sleeve 216 is formed of a desiccant entrained polymer to regulate the specific relative humidity within the container 200. As discussed above, forming the dividing walls 206 of a desiccant entrained polymer increases the exposed surface area of the desiccant entrained polymer, thereby improving humidity regulation within the container 200. Alternatively, the sleeve 216 is formed of a standard polymer and a desiccant is placed within the container 200.

The biasing element 218 is located between the spinner 210 and the sleeve 216. The biasing element 218 may be, for example, a coil spring which fits around the elongated shaft 226 of the spinner 210. The biasing element 218 applies a biasing force to press the spinner 210 in an upward direction (with reference to FIG. 5).

Figure 6:
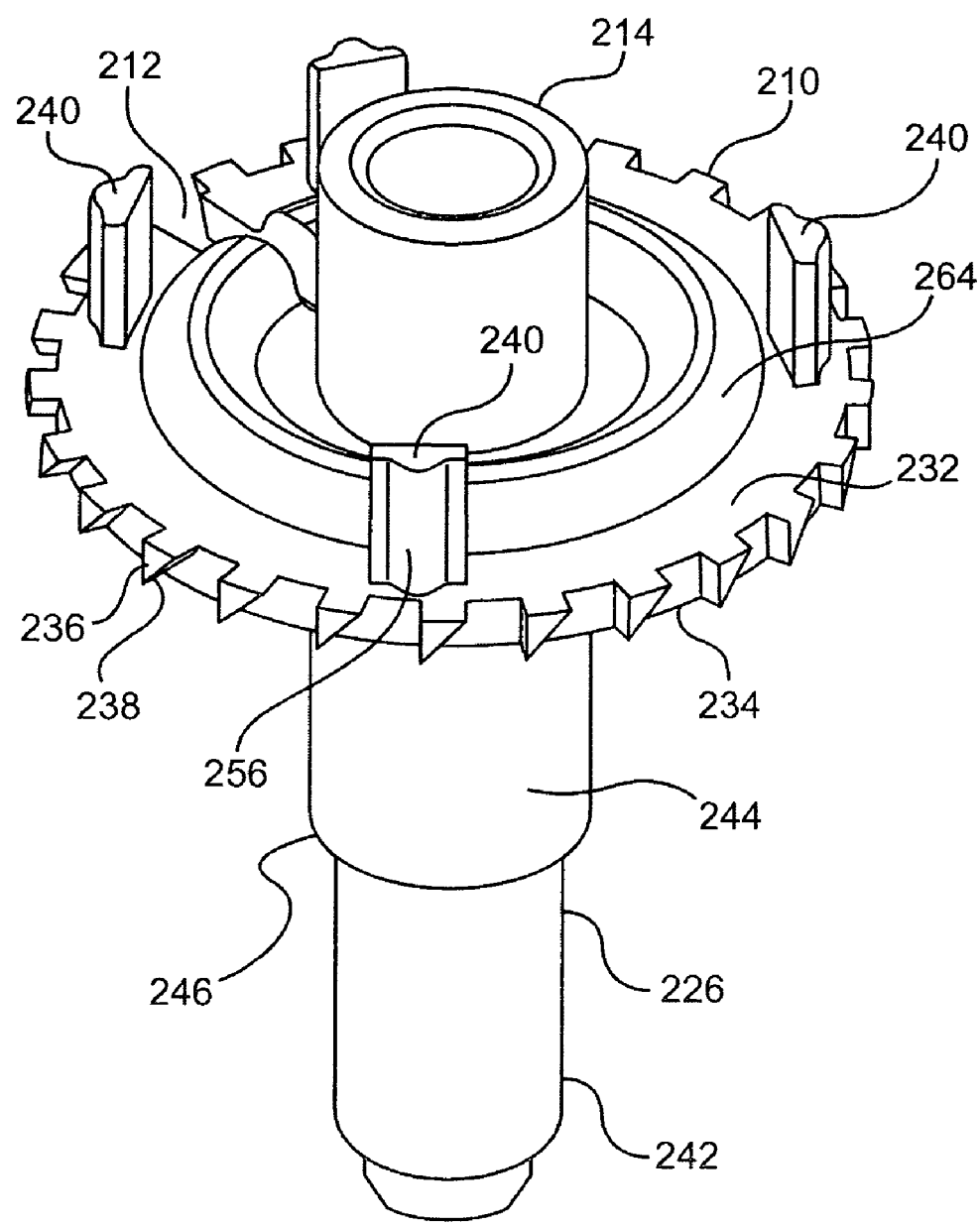
FIG. 6 is a perspective view of the spinner of the storage vial of FIG. 5.

As seen most clearly in FIG. 6, the spinner 210 has an upper surface 232 and a lower surface 234, and a cover opening 212 which extends through the spinner 210. The cover opening 212 is sized to allow one test strip to pass through the cover opening 212. A plurality of first cams 236 are located around the outer periphery of the spinner 210. The first cams 236 have first, angled cam surfaces 238.

The spinner 210 has at least one flexing beam 240 located on the upper surface 232 of the spinner 210. In the illustrated embodiment, four flexing beams 240 are provided. A pushbutton 214 is also provided on the upper surface 232 of the spinner 210.

A portion 264 of the spinner 210 may be formed of an optically transparent material so that a user may determine how many test strips are in the storage vial 200. The optically transparent portion 264 of the spinner 210 may be configured so that it magnifies the image being viewed, thus magnifying the edge of a strip.

An elongated shaft 226 is located on the lower surface 234 of the spinner 210. The elongated shaft 226 preferably has a first portion 242 with a first, smaller diameter, and a second portion 244 with a larger diameter. The transition area between the first and second portions 242, 244 forms a stop 246. The first portion 242 of the elongated shaft 226 is sized to fit within the recess 224 in the boss 222. The stop 246 prevents the spinner 210 from being pressed too far downward, as will be discussed in detail further below.

Figure 8:
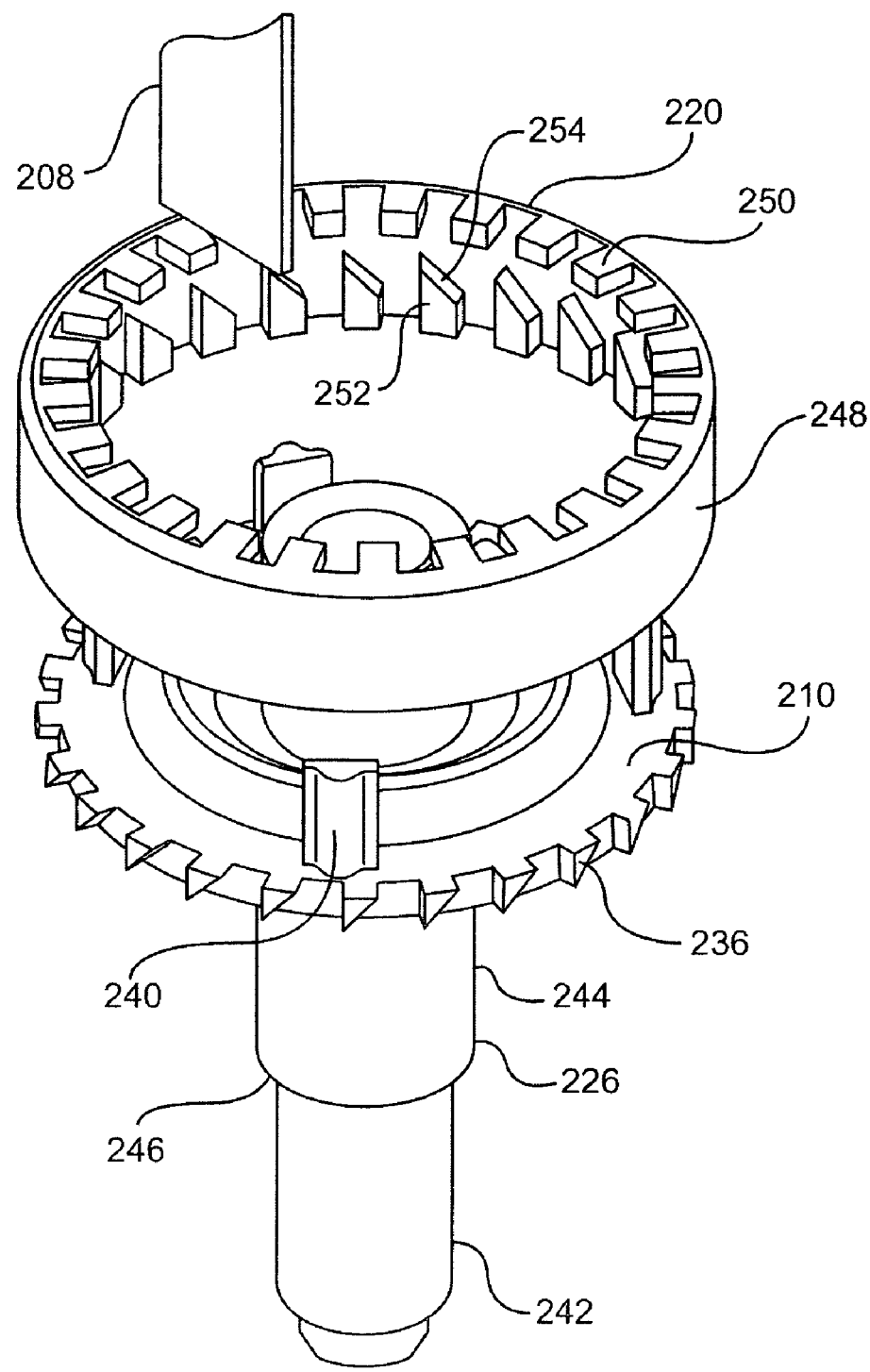
FIG. 8 is a perspective view of the cam sleeve and the spinner of the storage vial of FIG. 5.

Referring to FIG. 8, the cam sleeve 220 is a generally circular ring 248 which is sized to fit into the interior of the container 200. On its interior surface, the cam sleeve 220 has a plurality of cam teeth 250 250, and a plurality of second cams 252. The second cams 252 have second, angled cam surfaces 254 which cooperate with the first, angled cam surfaces 238, as will be discussed in detail below.

The spinner 210 and the cam sleeve 220 may be formed of a polymer or any other suitable material. They may also be formed of a desiccant entrained polymer, so long as the addition of the desiccant does not reduce the mechanical characteristics of the polymer enough to result in premature failure.

The method of using the storage vial 200 for storing and dispensing test strips according to the second exemplary embodiment of the invention will now be described. Initially, test strips are loaded into the radially extending slots 204 formed in the sleeve 216 so that one test strip is located in each slot 204. The sleeve 216 is then placed in the container 200. The biasing element 218 is placed around the elongated shaft 226 of the spinner 210, and the elongated shaft 226 is inserted into the boss 222 in the sleeve 216. The cam sleeve 220 is then placed into the container 200. Rotational alignment between the cam sleeve 220 and the slots 204 can be maintained during assembly by using keyways, visual alignment or other conventional methods. The teeth on the cam sleeve 220 overhang the spinner 210, so that the cam sleeve 220 retains all of the components within the container 200. The cam sleeve 220, in turn, is retained in the container 200 by an undercut in the container 200, or by affixing the cam sleeve 220 to the container 200 with adhesives, ultrasonic welding, or other conventional fixation methods. A replaceable lid (not shown but similar to the lid 114 of the previous embodiment) is then placed on the container 200 to form a substantially hermetic seal. The storage vial 200 may now be stored, and test strips will be protected from environmental hazards, such as moisture. Typically, these steps will be performed by a manufacturer, rather than an end user of the storage vial 200.

Figure 9:
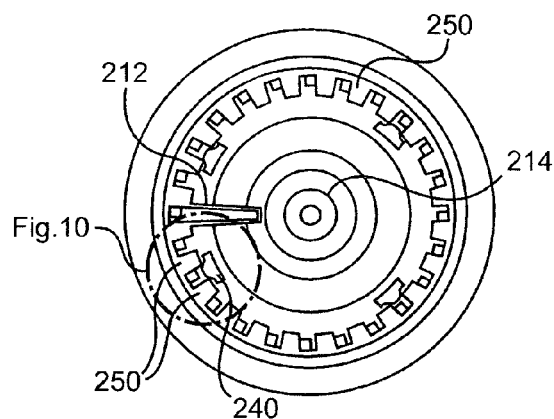
FIG. 9 is a top view showing the interaction between the cam sleeve and the spinner of the storage vial of FIG. 5.
Figure 10:
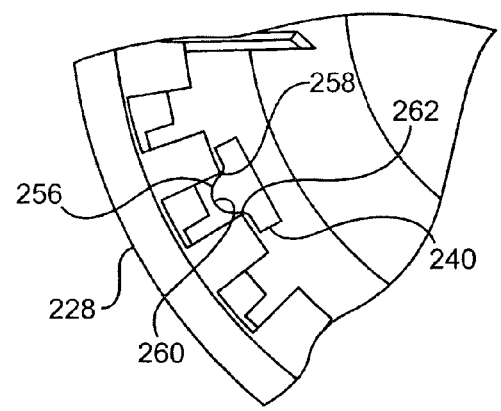
FIG. 10 is an enlarged view of the circled area in FIG. 9.

To dispense a test strip, a user opens the lid and pushes the pushbutton 214 to rotate the spinner 210 to the next slot 204. FIGS. 9-16 illustrate the operation of the spinner 210 in detail. Initially, as seen in FIG. 13, before a user presses the pushbutton 214, the first cams 236 on the spinner 210 are disposed above the second cams 252 on the cam sleeve 220 due to the biasing force of the biasing element 218. And, as seen in FIGS. 9, 10, and 13, the flexing beams 240 are seated within the cam teeth 250. The flexing beams 240 prevent the spinner 210 from freely rotating, and align the cover opening 212 with one of the plurality of slots 204.

Figure 13:
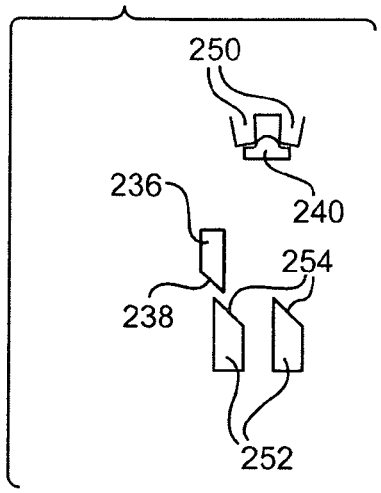
FIGS. 13-16 are diagrams showing the operation of the storage vial of FIG. 5.
Figure 14:
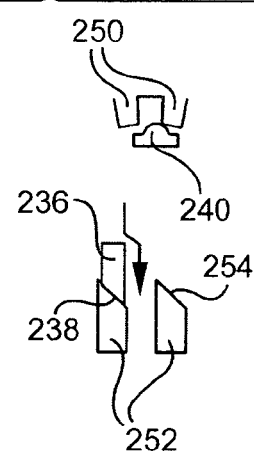

When a user begins to press the pushbutton 214 on the spinner 210 and overcomes the biasing force of the biasing element 218, the spinner 210 is pressed lower into the container 200. Thus, as seen in FIG. 14, the first cam surfaces 238 begin to engage the second cam surfaces 254. Since the second cam surfaces 254 are fixed with respect to the container 200, the contact between the first cam surfaces 238 and the second cam surfaces 254 causes the first cam surfaces 238 to move towards the right (with reference to the illustrations), thereby causing the spinner 210 to begin to rotate in a forward direction. At this time, the flexing beams 240 also begin to flex to pass by the cam teeth 250 located on the cam sleeve 220. If the pushbutton is released at this point, the interaction of the flexing beams 240 with the cam teeth 250 will restore the spinner 210 to the original position shown in FIG. 13. This is because the surfaces 256 of the flexing beams 240 that contact the cam teeth 250 are rounded and have an ascending portion 258, a top 260, and a descending portion 262. At this initial stage, the cam teeth 250 have not passed the tops 260 of the rounded surfaces 256, and the ascending portions 258 of the rounded surfaces 256 of the flexing beams 240 engages the cam teeth 250 and generate a force in a reverse direction (i.e., a leftward direction).

Figure 11:
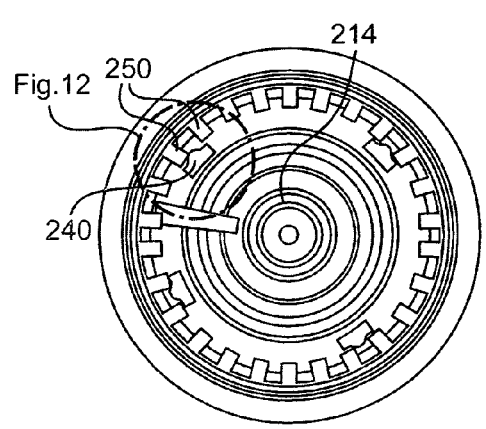
FIG. 11 is another top view showing the interaction between the cam sleeve and the spinner of the storage vial of FIG. 5.
Figure 12:
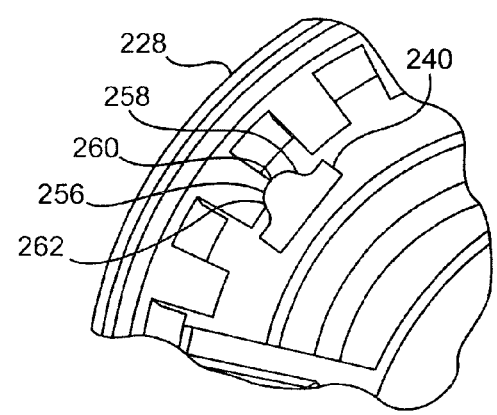
FIG. 12 is an enlarged view of the circled area in FIG. 11.
Figure 15:
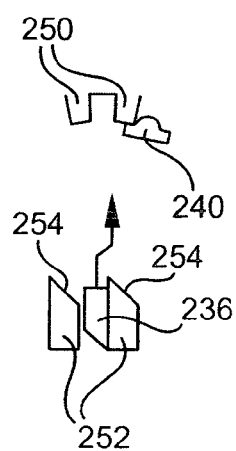

If a user continues to press the pushbutton, however, the spinner 210 continues to rotate, and the tops 260 of the rounded surfaces 256 of the flexing beams 240 pass by the cam teeth 250, as illustrated in FIGS. 11, 12, and 15. At this position, the descending portions 262 of the rounded surfaces 256 of the flexing beams 240 generate a force in a forward direction (i.e. a rightward direction). Thus, as shown in FIG. 15, the first cams 236 contact the second cams 252, so that the rotation of the spinner 210 is restricted. At this point, the stop 246 on the spinner 210 engages the boss 222 to prevent the spinner 210 from being pressed further into the housing.

Figure 16:
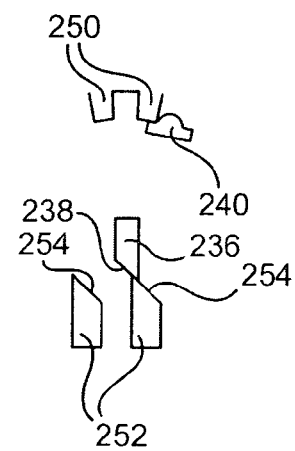

Finally, when the user releases the pushbutton 214, the biasing element 218 urges the spinner 210 upward. The first cams 236 are disengaged from the second cams 254, and the descending portions 262 of the rounded surfaces 256 of the flexing beams 240 interact with the cam teeth 250 to generate a force which rotates the spinner 210 in a forward direction so that the cover opening 212 is aligned with the next slot 204, as shown in FIG. 16. Thus, the flexing beams 240 ensure that the spinner 210 is completely rotated to the next slot 204 so that the cover opening 212 is aligned with the next slot 204.

After the cover opening 212 is aligned with a slot 204 containing a test strip, the user inverts the container 202. A test strip located within the slot 204 is dispensed through the cover opening 212 with the aid of gravity. The user may then grasp the exposed test strip to withdraw the test strip from the container 200 and use the test strip.

To dispense another test strip, the user rotates the cover 210 again by pressing the pushbutton 214 on the spinner 210. After dispensing the desired number of test strips, the user may then replace the lid on the container 200 to store the remaining test strips for future use.

After all of the stored test strips stored in the container 202 have been dispensed, the storage vial 200 may be discarded, or may be returned to the manufacturer for recycling. Reusable embodiments of the container 102 are also within the scope of the present invention.

While various embodiments have been chosen to illustrate the invention, it will be understood by those skilled in the art that various changes and modifications can be made therein without departing from the scope of the invention as defined in the appended claims.

What is claimed is:

1. An apparatus for dispensing test strips, comprising:
a container including an outer wall;
a plurality of radially extending slots formed by a plurality of dividing walls, each slot sized to receive a single test strip;
a rotatably positionable cover carried by the container for covering the plurality of radially extending slots, the cover including an opening and a spinner that includes a first set of cam surfaces; and
a cam sleeve with a second set of cam surfaces operatively engageable with the first set of cam surfaces to rotate the spinner;
wherein when the cover rotates, the cover opening aligns with one of the slots at a time to allow removal of a single test strip located within a respective slot.

2. The apparatus of claim 1, further comprising a boss centrally disposed within the container, the boss including a recess.

3. The apparatus of claim 2, wherein the cover comprises an upper surface and a lower surface, and the lower surface of the cover comprises an elongated shaft positioned within the recess of the boss.

4. The apparatus claim 3, wherein the upper surface of the cover comprises a handle.

5. The apparatus of claim 3, wherein the lower surface of the cover further comprises a plurality of detents that engage the plurality of dividing walls to control rotation of the cover.

6. The apparatus of claim 1, wherein the plurality of dividing walls extend radially inwardly from the outer wall of the container toward the center of the container.

7. The apparatus of claim 1, further comprising a sleeve forming the plurality of dividing walls.

8. The apparatus of claim 1, wherein the spinner comprises at least one flexing beam.

9. The apparatus of claim 8, wherein the cam sleeve has teeth which engage the at least one flexing beam to control rotation of the spinner.

10. The apparatus of claim 1, further comprising a spring which biases the spinner.

11. The apparatus of claim 1, wherein the spinner includes a portion composed of an optically clear material.

12. The apparatus of claim 1, wherein the spinner has an elongated shaft including a stop.

13. The apparatus of claim 12, further comprising:
a boss centrally disposed within the container, the boss including a recess for receiving the elongated shaft of the spinner, the stop on the spinner contacting the boss to control movement of the spinner.

14. An apparatus for dispensing test strips, comprising:
a vial with a plurality of radially extending slots, each slot adapted to store a test strip;
means for selectively exposing one of the plurality of radially extending slots to dispense a test strip stored in the exposed slot and for covering the remaining slots;
means for actuating the means for selectively exposing one of the plurality of radially extending slots;
wherein the means for selectively exposing one of the plurality of radially extending slots comprises a spinner with a slot which exposes one of the plurality of radially extending slots, the spinner having a pushbutton; and
the means for actuating the means for selectively exposing one of the plurality of radially extending slots comprises:
a plurality of first cam surfaces formed on the spinner; and
a cam sleeve comprising a plurality of second cam surfaces, the second cam surfaces interacting with the first cam surfaces so that when the pushbutton is pressed, the first cam surfaces engage the second cam surfaces to cause the spinner to rotate.

15. The apparatus of claim 14, wherein the means for selectively exposing one of the plurality of radially extending slots comprises a cover with a slot which exposes one of the plurality of radially extending slots.

16. The apparatus of claim 15, further comprising means for actuating the means for exposing one of the plurality of radially extending slots.

17. The apparatus of claim 16, wherein the means for actuating the means for exposing one of the plurality of radially extending slots comprises a handle attached to the cover.

18. The apparatus of claim 14, wherein:
the cam sleeve further comprises a plurality of teeth; and
the spinner further comprises at least one flexing beam, the flexing beam interacting with the plurality of teeth to control movement of the spinner.

19. The apparatus of claim 14, wherein:
the container further comprises a boss with a recess; and
the spinner further comprises a shaft with a stop located in the recess, the stop controlling the movement of the spinner.

* * * * *

UNITED STATES PATENT AND TRADEMARK OFFICE
CERTIFICATE OF CORRECTION

PATENT NO. : 7,597,853 B2  Page 1 of 1
APPLICATION NO. : 11/430179
DATED : October 6, 2009
INVENTOR(S) : West et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 614 days.

Signed and Sealed this

Twenty-eighth Day of September, 2010

David J. Kappos
*Director of the United States Patent and Trademark Office*